US010716530B2

(12) United States Patent
Chang et al.

(10) Patent No.: US 10,716,530 B2
(45) Date of Patent: Jul. 21, 2020

(54) METHOD AND SYSTEM OF AUTOMATED X-RAY POSITIONING AND COLLIMATION CONTROL ON HAND AND FOOT SCAN

(71) Applicant: Siemens Healthcare GmbH, Erlangen (DE)

(72) Inventors: Yao-jen Chang, Princeton, NJ (US); Birgi Tamersoy, Erlangen (DE); Susanne Oepping, Erlangen (DE); Ralf Nanke, Neunkirchen (DE); Terrence Chen, Princeton, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 134 days.

(21) Appl. No.: 15/950,598

(22) Filed: Apr. 11, 2018

(65) Prior Publication Data

US 2018/0296178 A1     Oct. 18, 2018

(30) Foreign Application Priority Data

Apr. 13, 2017 (EP) .................................... 17166493

(51) Int. Cl.
*G01N 23/04*     (2018.01)
*A61B 6/00*     (2006.01)
(Continued)

(52) U.S. Cl.
CPC ............... *A61B 6/545* (2013.01); *A61B 6/06* (2013.01); *A61B 6/08* (2013.01); *A61B 6/40* (2013.01);
(Continued)

(58) Field of Classification Search
CPC ..... A61B 6/06; A61B 6/08; A61B 6/40; A61B 6/5211; A61B 6/5294; A61B 6/542; A61B 6/545; A61B 6/544; A61B 6/547; A61B 6/032; A61B 5/0077; A61B 6/0457; A61B 6/469; A61B 6/488; A61B 6/54; A61B 5/1079; A61B 6/4464; A61B 6/5205; A61B 6/0407; A61B 6/0492; A61B 6/4452;
(Continued)

(56) References Cited

U.S. PATENT DOCUMENTS 7,869,568 B2    1/2011   Yokoyama et al.
8,696,200 B2    4/2014   Mohr
(Continued)

FOREIGN PATENT DOCUMENTS

EP         2954843 A1    12/2015
WO     2005009243 A1    2/2005
WO     2014033614 A1    3/2014

*Primary Examiner* — Irakli Kiknadze

(57) ABSTRACT

An automation method is disclosed for an X-ray tube scanner having an X-ray tube and an X-ray detector. The method allows the X-ray tube scanner to detect the X-ray detector's plane with an object to be imaged placed on the X-ray detector; determine a boundary box of the object to be imaged on the X-ray detector; determine the object's center position and orientation on the X-ray detector's plane; transfer the object's center position from the object's coordinate system to the X-ray tube's coordinate system; and estimate the X-ray tube control parameters for aligning the X-ray field emitted from the X-ray tube's collimator to the object's center position and the object's orientation on the X-ray detector.

15 Claims, 10 Drawing Sheets

(51) Int. Cl.
*A61B 6/06* (2006.01)
*A61B 6/08* (2006.01)
*G06T 7/73* (2017.01)
*G06T 7/00* (2017.01)

(52) U.S. Cl.
CPC .......... *A61B 6/5211* (2013.01); *A61B 6/5294* (2013.01); *G06T 7/0012* (2013.01); *G06T 7/73* (2017.01); *A61B 6/542* (2013.01); *G06T 2207/10028* (2013.01); *G06T 2207/10116* (2013.01); *G06T 2207/30004* (2013.01)

(58) Field of Classification Search
CPC ........ A61B 5/0075; G06T 2207/10028; G06T 2207/10116; G06T 2207/30004; G06T 7/0012; G06T 7/73; G06T 11/006; G06T 2207/30008; G06T 2210/41; G06T 2207/10016; G06T 2207/30232; G06T 7/194; G06T 7/246; G06T 7/11; G06T 2207/30241; G06T 7/254; G06T 2210/12; G06T 2207/10024; G06T 7/20; G06T 2207/30196; G06T 7/248; G06T 7/70; G06T 7/90; G06T 2207/20036; G06T 2207/20224; G06T 7/25; G06K 2209/055; G06K 9/00208; A61N 2005/1087; A61N 2005/1088; A61N 5/103; G21K 1/08; G21K 5/04
USPC .......................................... 378/62, 205–207
See application file for complete search history.

(56) References Cited

U.S. PATENT DOCUMENTS

| | | | |
|---|---|---|---|
| 9,028,144 B2 | 5/2015 | Choi et al. | |
| 9,134,436 B2 | 9/2015 | Kwak et al. | |
| 9,280,837 B2 * | 3/2016 | Grass | A61B 6/4441 |
| 2015/0104092 A1 | 4/2015 | Flohr et al. | |
| 2015/0185340 A1 * | 7/2015 | Ye | A61B 6/0492 |
| | | | 378/206 |
| 2016/0374639 A1 | 12/2016 | Becker et al. | |
| 2017/0055925 A1 * | 3/2017 | Lee | A61B 6/465 |
| 2017/0100089 A1 | 4/2017 | Chang et al. | |
| 2017/0323443 A1 * | 11/2017 | Dhruwdas | G06K 9/00208 |

* cited by examiner

METHOD AND SYSTEM OF AUTOMATED X-RAY POSITIONING AND COLLIMATION CONTROL ON HAND AND FOOT SCAN

CROSS-REFERENCE TO RELATED APPLICATIONS

This application claims priority under 35 U.S.C. § 119(a) to European Patent Application No. EP17166493, filed Apr. 13, 2017, the entire contents of which are incorporated by reference herein.

FIELD

The present disclosure relates to scanner automation for X-ray image acquisition, and more particularly, to X-ray tube scanner automation for hand and foot scanning.

BACKGROUND

X-ray scanning is typically performed by a technician manually positioning an X-ray tube to focus the X-ray scan on a region of interest on a patient. The positioning and orientation of the X-ray tube with respect to the patient relies on the technician's subjective decisions, which often leads to inconsistency between different X-ray scans. Thus, X-ray scanner automation is desired for improving the scanning workflow efficiency as well as scanned image quality as compared with X-ray scans obtained by technicians manually positioning the X-ray tube.

SUMMARY

The present disclosure provides a method and system for X-ray tube scanner automation for scanning a patient's body portion such as a hand or a foot. The method allows the X-ray tube scanner to detect the X-ray detector's plane with an object to be imaged placed on the X-ray detector; determine a boundary box of the object to be imaged on the X-ray detector; determine the object's center position and orientation on the X-ray detector's plane; transfer the object's center position from the object's coordinate system to the X-ray tube's coordinate system; and estimate the X-ray tube control parameters for aligning the X-ray field emitted from the X-ray tube's collimator to the object's center position and/or orientation on the X-ray detector.

An X-ray tube scanner system comprising an X-ray tube, an X-ray detector, and a system controller is also disclosed where the system controller comprises a processor, and a non-transitory computer readable medium storing computer program instructions for operating the X-ray tube scanner. The computer program instructions when executed by the processor cause the processor to perform the automation method for the X-ray tube scanner system disclosed herein.

These and other advantages of the invention will be apparent to those of ordinary skill in the art by reference to the following detailed description and the accompanying drawings.

DETAILED DESCRIPTION

Figure 1:
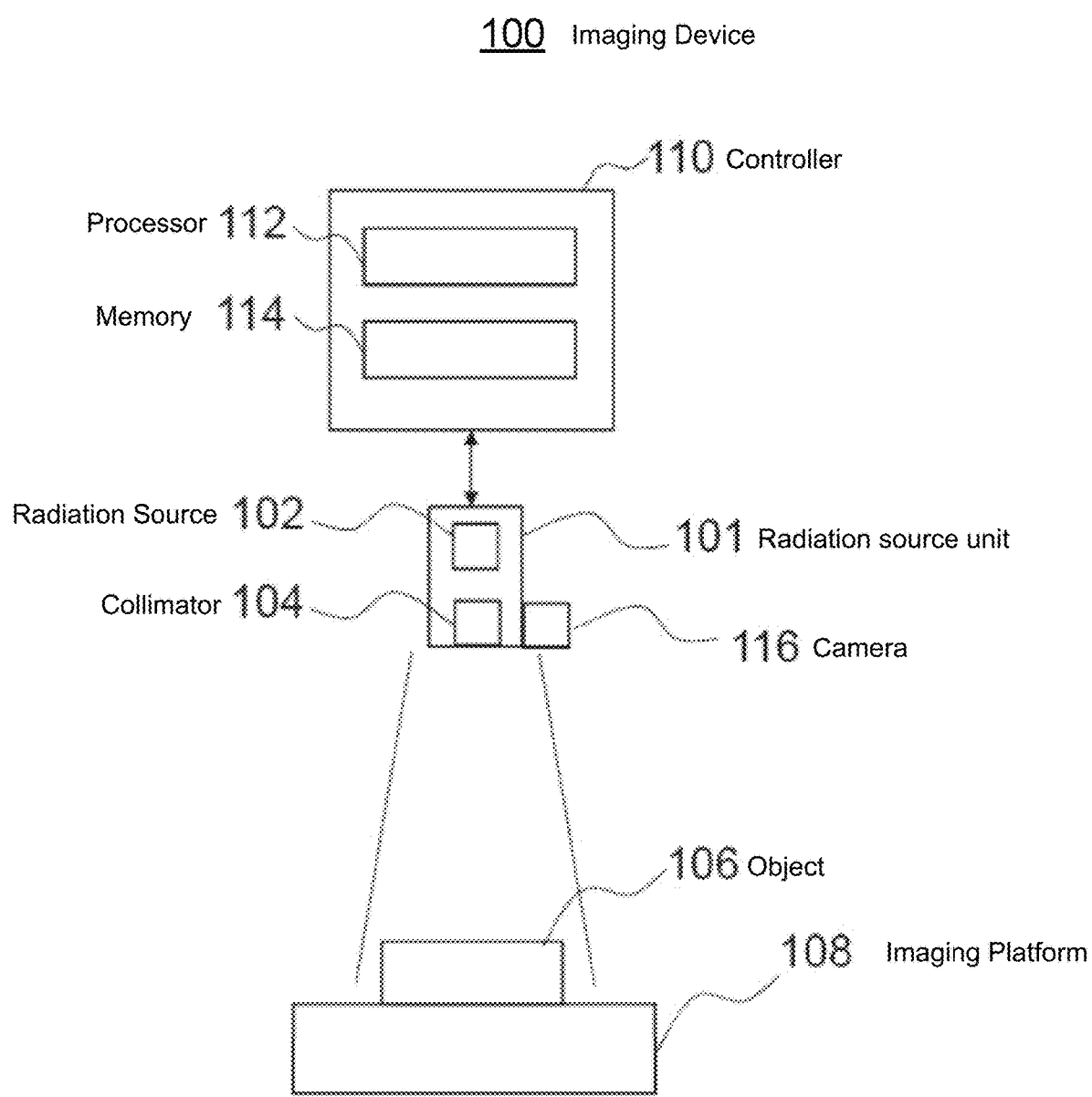
FIG. 1 shows a medical imaging device according to one aspect of the present disclosure.

The present disclosure relates in one aspect to a method controlling one or more parameters of a medical imaging device comprising a radiation source. In another aspect, the present disclosure relates to a medical imaging device. In further aspects, this disclosure relates to a computer program product and a computer-readable medium.

Medical images devices, such as X-ray imaging devices, may provide flexibility and convenience for medical imaging because the radiation source can be moved freely to focus on a region of interest on an object to be imaged, such as a body part of a patient.

Conventionally, adjustment of a collimator for collimating the radiation beam and positioning of the radiation source, is performed manually. In known imaging devices, a technician moves, for example, an X-ray tube and aligns a radiation field projected from the collimator to the object center and then adjusts the light field size to match the size of a region of the body part to be imaged. Typically, several iterations of manual adjustment may be needed, which may be time consuming.

Therefore, there is a need to automate the process to improve throughput and the efficiency of such imaging devices.

The present disclosure relates in one aspect to a method of controlling one or more parameters of a medical imaging device comprising a radiation source unit, the method comprising:

receiving image data representing a first image of an object to be imaged using the radiation source unit to form a second image;

detecting a plurality of positions of respective predetermined features in the first image;

determining a boundary box of an imaging area of the object to be imaged on the basis of the detected positions; and controlling one or more parameters of the radiation source unit on the basis of the determined boundary box.

One embodiment of the invention relates in one aspect to a method, the method comprising:
determining an object size and/or an object orientation of the object to be imaged on the basis of the detected positions.

One embodiment of the invention relates in one aspect to a method, the method comprising:
determining the object orientation on the basis of an angle of a line intersecting two or more of the detected positions; and
orientating the boundary box of the imaging area of the object to correspond with the object orientation.

One embodiment of the invention relates in one aspect to a method, wherein the one or more parameters of the radiation source unit comprise a position and/or an orientation of the radiation source unit and/or one or more collimator settings of a collimator of the radiation source unit.

One embodiment of the invention relates in one aspect to a method, wherein detecting the positions comprises:
evaluating one or more portions of the first image with respect to a model of predetermined features;
assigning a probability value to each of the one or more portions of the first image on the basis of the evaluation; and
determining that one or more of the one or more portions of the first image corresponds with a said predetermined feature on the basis of the corresponding assigned probability value.

One embodiment of the invention relates in one aspect to a method, the method comprising:
identifying a background portion of the first image and a foreground portion of the first image based on data in the received image data representing one or more image channels; and
determining the boundary box on the basis of the identifying.

One embodiment of the invention relates in one aspect to a method, the method comprising:
determining whether a first part of the foreground portion of the first image meets the boundary box; and
if the first part of the foreground portion of the first image meets the boundary box, adjusting the boundary box to encompass the first part.

One embodiment of the invention relates in one aspect to a method, the method comprising:
determining whether there is a background portion of the first image between the first part of the first image and the boundary box; and
if there is a background portion of the first image be-tween the first part of the first image and the boundary box, adjusting the boundary box so as to reduce the size of the background portion.

One embodiment of the invention relates in one aspect to a method, wherein the object to be imaged is a body part of a human or animal subject and the predetermined features comprise anatomical features of the subject and the first part comprises a distal end of the object to be imaged.

The invention relates in one aspect to a medical imaging device comprising:
a processor arranged to:
receive image data representing a first image of an object to be imaged using a radiation source unit of the medical imaging device;
determine a boundary box of an imaging area of the object to be imaged on the basis of detected positions of respective predetermined features in the first image; and
control one or more parameters of the radiation source unit on the basis of the determined boundary box.

One embodiment of the invention relates in one aspect to a medical imaging device, wherein the one or more parameters comprise a position and/or orientation of the radiation source unit.

One embodiment of the invention relates in one aspect to a medical imaging device, wherein the radiation source unit comprises a collimator for collimating a beam of radiation emitted from the radiation source unit, wherein the processor is arranged to control one or more collimator settings on the basis of the determined boundary box.

One embodiment of the invention relates in one aspect to a medical imaging device, comprising a camera arranged to generate the first image, the camera being different from the radiation source unit.

One embodiment of the invention relates in one aspect to a medical imaging device, wherein the medical imaging device is an X-ray radiography device and the radiation source unit comprises an X-ray source.

The invention relates in one aspect to a computer program product comprising a computer program, the computer pro-gram being loadable into a memory unit of a data processing system, including program code sections to make the data processing system execute the method according to an aspect of the invention when the computer program is executed in said data processing system.

The computer program product can be, for example, a computer program or comprise another element apart from the computer program. This other element can be hardware, for example a memory device, on which the computer program is stored, a hardware key for using the computer program and the like, and/or software, for example a documentation or a software key for using the computer program.

The medical imaging device can be, for example, be selected from the group consisting of a computed tomography de-vice, a magnetic resonance imaging device, a molecular imaging device, a SPECT-device, a PET-device and combinations thereof. The medical imaging device can be, for example, a combination of an imaging modality and a therapy modality, in particular a radiation therapy modality.

Reference is made to the fact that the described methods and the described medical imaging device are merely preferred example embodiments of the invention and that the invention can be varied by a person skilled in the art, without departing from the scope of the invention provided it is specified by the claims.

FIG. 1 is a diagram illustrating an imaging device 100 according to an embodiment of the present disclosure. The imaging device comprises a radiation source unit 101 comprising a radiation source 102 arranged to emit a beam of radiation through a collimator 104. The collimator 104 is arranged to collimate the beam of radiation. For example, the collimator 104 may be arranged to restrict a spatial extent of the radiation beam in one or more directions perpendicular to a direction of propagation of the beam.

In some embodiments, the imaging device 100 is an X-ray tube scanner and the radiation source unit 101 is an X-ray tube. The radiation source 102 may, for example, be a source of high energy electromagnetic radiation. For example, the radiation source 102 may be an X-ray generator arranged to emit X-ray radiation.

The radiation source 102 is arranged to be moveable such that the beam of radiation may be directed at an object 106 to be imaged. The collimator 104 may be adjustable such that the extent of the beam may cover more or less of the object 106.

The object 106 is positioned on the surface of an imaging platform 108. The imaging platform 108 is, for example, an X-ray detector arranged to detect radiation emitted from the radiation source 102 or be configured to receive such a detector. In other examples, the imaging platform 108 may be arranged to receive a cassette containing radiographic or photographic film reactive to the radiation emitted from the radiation source 102.

The imaging device 100 may comprise a controller 110 for controlling one or more parameters of the radiation source unit 101. For example, the controller 110 may control a position and/or an orientation of the radiation source unit 101 to control a position from which radiation is emitted from the radiation 102 and/or one or more settings of the collimator 104. For example, the controller 110 may be arranged to generate control signals for controlling drive motors or other electromechanical actuators connected to the radiation source unit 101 and/or the collimator 104 to control the position orientation, and/or extent of an emitted beam of radiation.

The controller 110 may be implemented using hardware and/or software. In some examples, the controller 110 may comprise a processor 112 programmed to perform the functions of the controller 110.

The controller 110 may include a memory 114 arranged to store data in the form of a model that is trained by implementing a machine learning algorithm prior to installation and use of the imaging device 100 in an operation setting. For example, the model may be trained by supplying sample images to the model and, with input from a human operator, the machine learning algorithm may learn to detect features in the sample data. In some examples, the available sample data may be augmented by rotating and/or flipping the sample images.

Furthermore, the memory 114 may store a computer program executable by the processor 112, to perform the methods described herein, and specifically the methods described below with reference to FIGS. 2 and 4.

The memory 114, may be any suitable form of memory. For example, the memory 114 may comprise volatile memory, such as random access memory (RAM) and/or non-volatile memory such as read only memory (ROM) or flash memory. Further-more, the memory 114 might comprise multiple, separate, memory devices and may comprise a combination of volatile and non-volatile memory. In some examples, certain component of the invention, such as the computer program and/or the model, may be stored in one memory device, while other components may be stored in another memory device.

The machine learning algorithm may be any suitable algorithm. For example, the machine learning algorithm may be a probabilistic boosting tree (PBT) algorithm, which enables a model to be trained to detect an object in an image and to detect positions of predetermined features (i.e. landmarks) in the image, or a model to be trained to detect the center, size, and orientation of a specific object.

In another implementation, the machine learning algorithm may be a convolutional neural network (CNN) algorithm, which enables a model to be trained to detect an object in an image, to classify the detected object (i.e. identify an object type) and to detect the center, size, and orientation of the object in the image. So, for example, the controller 110 may classify whether the foreground object is from left hand, right hand, left foot, or right foot.

In some examples, information regarding the type of object (e.g. that the object is a human hand or foot) may be provided to the machine learning algorithm by a human operator in order to select the model for detecting a specific object. In other examples, information regarding the type of object may not be input by a human operator and may instead be learned or inferred by the model.

In some embodiments, as depicted in FIG. 1, the imaging device 100 comprises a camera 116, such as, for example, an optical camera. For example, the camera 116 may be a 2D camera arranged to provide one or more color channels or a 2D camera arranged to provide a grayscale image. In other examples, the camera 116 may be a 3D camera arranged to provide one or more color channels and one or more depth channels. In some embodiments, the imaging device 100 may comprise one or more interfaces (not shown) for receiving a connection to a camera not permanently connected to the imaging device 100.

The camera 116 may be mechanically connected to the radiation source unit 101, as shown in FIG. 1, so that the camera 116 moves with the radiation source unit 101. Accordingly, images generated by the camera 116 will include an area that will be irradiated by radiation source 102 wherever the radiation source unit 101 is located.

Figure 2:
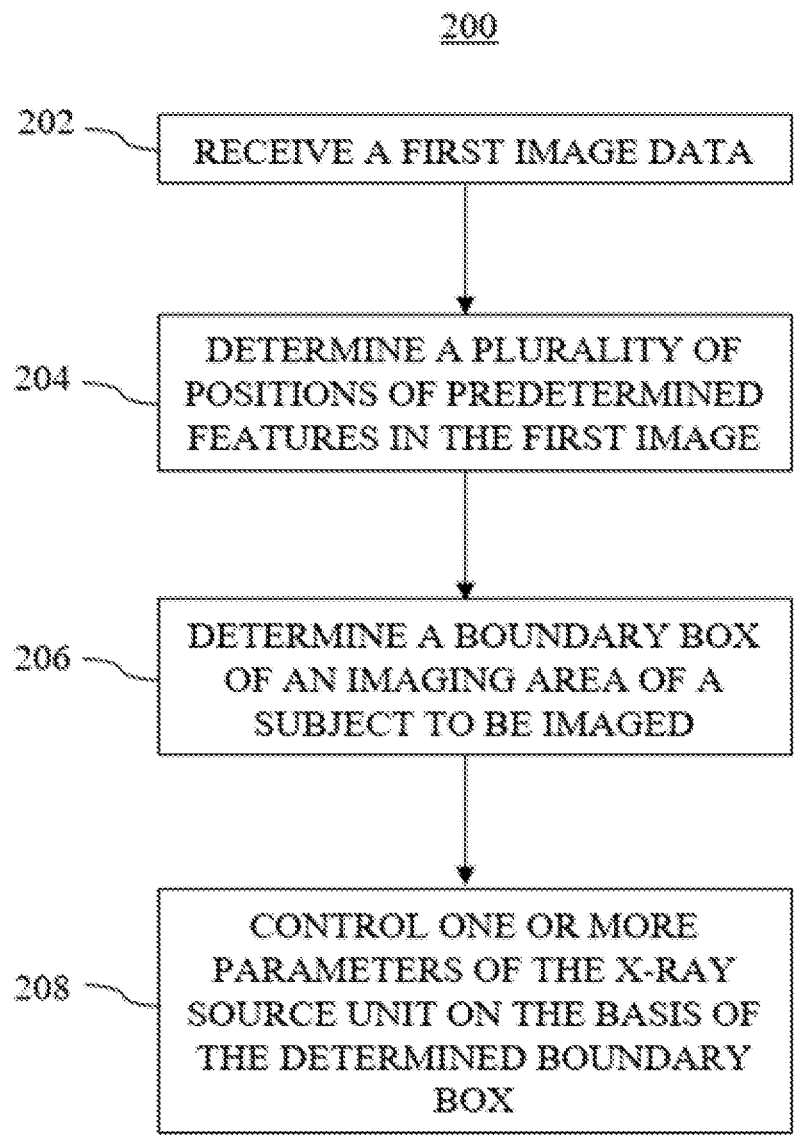
FIG. 2 shows a workflow diagram illustrating a method according to one aspect of the present disclosure.

FIG. 2 is a flow diagram depicting a method 200 of controlling one or more parameters of the medical imaging device 100. The method 200 may, for example, be implemented by software or firmware executed by the controller 110 described above with reference to FIG. 1.

At block 202, the controller 110 receives image data representing a first image of the object 106 to be imaged using the radiation source to form a second image. For example, the image data representing the first image of the object is received from the camera 116.

At block 204, the controller 110 determines a plurality of positions of predetermined features in the first image. For example, the controller 110 may evaluate one or more portions of the first image with respect to a model of positions of predetermined features. In some examples, the controller 110 may evaluate regions of the first image comprising one or more pixels. The regions of the first image may be defined by a moving window, for example. Based on the evaluation with respect to the model, the controller 110 may assign, to each of the one or more portions of the first image, a probability value relating to a probability that a given portion of the image corresponds to a position of a predetermined feature. Once each portion of the first image is assigned a probability value, the controller 110 may determine that one or more of the one or more portions of the first image corresponds with a position of a predetermined feature based on the corresponding assigned probability values. For example, portions of the first image with a probability value exceeding a threshold probability value may be identified as a position of a predetermined feature. Alternatively, portions of the first image with a highest probability value of relating to a particular type of predetermined feature may be identified as position of the predetermined features. For example, a portion of the image with the highest probability value of being knuckle may be identified as one position of a predefined feature and a portion of the image with the highest probability value of being wrist may be identified as another position of a predefined feature.

The predetermined features may be, for example, landmarks of the object 106 to be imaged, as defined when the model is trained, as described above, by supplying sample images to the model with input from a human operator. In some examples, the predetermined features may be anatomical features (i.e. body parts) of a human or animal subject.

For example, the positions of predetermined features may correspond to a wrist, an ankle, a finger, a toe, a joint, or any other body part.

In order to assist the controller 110 in determining the positions of predetermined features, in some examples an operator of the imaging device 100 may provide additional input via an interface device such as a keyboard, mouse, or touch-screen device (not shown) to indicate to the controller 110 the classification of the object 106 that is to be imaged. For example, the operator may provide input indicating that the object 106 to be imaged is a human hand or a human foot. In some examples, the controller 110 may use this additional input in the determining the predetermined features by, for example, considering in the evaluation with respect to the model, only sample data relevant to an object type corresponding with the object type defined by the additional input of the operator. By the operator providing such information, the computation burden placed on the controller may be reduced.

In particular, in some example, the controller 110 may request via a user interface (not shown) input, from the operator of the imaging device 100, specifying the type of object 106 to be imaged. However, in other examples, the controller 110 may determine the type of object without input from the operator of the imaging device 100, which may reduce the burden on the operator of the imaging de-vice 100.

At block 206, the controller 110 determines a boundary box of an imaging area of the object 106 to be imaged on the basis of the detected positions of predetermined features.

In some examples, the controller 110 may determine a size and/or an orientation of an object 106 to be imaged based on the detected positions of predetermined features. For example, the controller 110 may determine, based on the positions of known landmarks or features in the image (and perhaps information regarding the type of the object in the image), that the object 106 is likely to be a certain size and is at a certain orientation.

For example, the controller 110 may determine an angle of a line intersecting two (or more) positions of predetermined features and determine the orientation of the object 106 in the image based on the angle of that line. In some examples, the controller 110 may rotate the first image to align the first image according to an axis of the object 106 to be imaged. For example, in the case where the object 106 to be imaged is a human hand, the first image may be rotated such that a longitudinal axis of the hand, as defined by a line joining the knuckle joint of the middle finger with the center of the wrist, is parallel with an edge of a subsequently applied boundary box. In another example, in the case where the object 106 to be imaged is a human foot, the first image may be rotated such that a longitudinal axis of the foot, as defined by a line joining the joint the joint of the middle toe and the ankle, is parallel with an edge of a subsequently applied boundary box.

Alternatively, the controller 110 may orientate the boundary box of the imaging area to align the boundary box with an axis of the object 106 to be imaged. For example, in the case where the object 106 to be imaged is a human hand, an edge of the boundary box may be arranged to be parallel with a longitudinal axis of the hand, as defined by a line joining predetermined features at the knuckle joint of the middle finger with the center of the wrist.

At block 208, the controller 110 controls one or more parameters of the radiation source unit 101 on the basis of the determined boundary box. For example, the controller 110 may determine a mapping between parameters defining the boundary box and one or more parameters of the radiation source unit 101. For example, the controller 110 may determine a position and/or orientation of the radiation source unit 101 based on a mapping of the position of the boundary box and/or the controller 110 may determine one or more collimator settings of the collimator 105 based on a mapping of one or more edges of the boundary box.

The one or more parameters of the radiation source unit 101 may include a position and/or orientation of the radiation source unit 101 and/or one or more settings of the collimator 104. These parameters may be set such that the area of the object 106 exposed to radiation from the radiation source 102 is the area enclosed by the boundary box. In other examples, the one or more parameters of the radiation source unit 101 may include a relative position of the radiation source with respect to the object 106 to be imaged. For example, in some applications, such as fluoroscopy, the radiation source unit 101 may be fixed and the object 106 to be imaged may located on a table that is moveable relative to the radiation source 102.

Figure 3A:
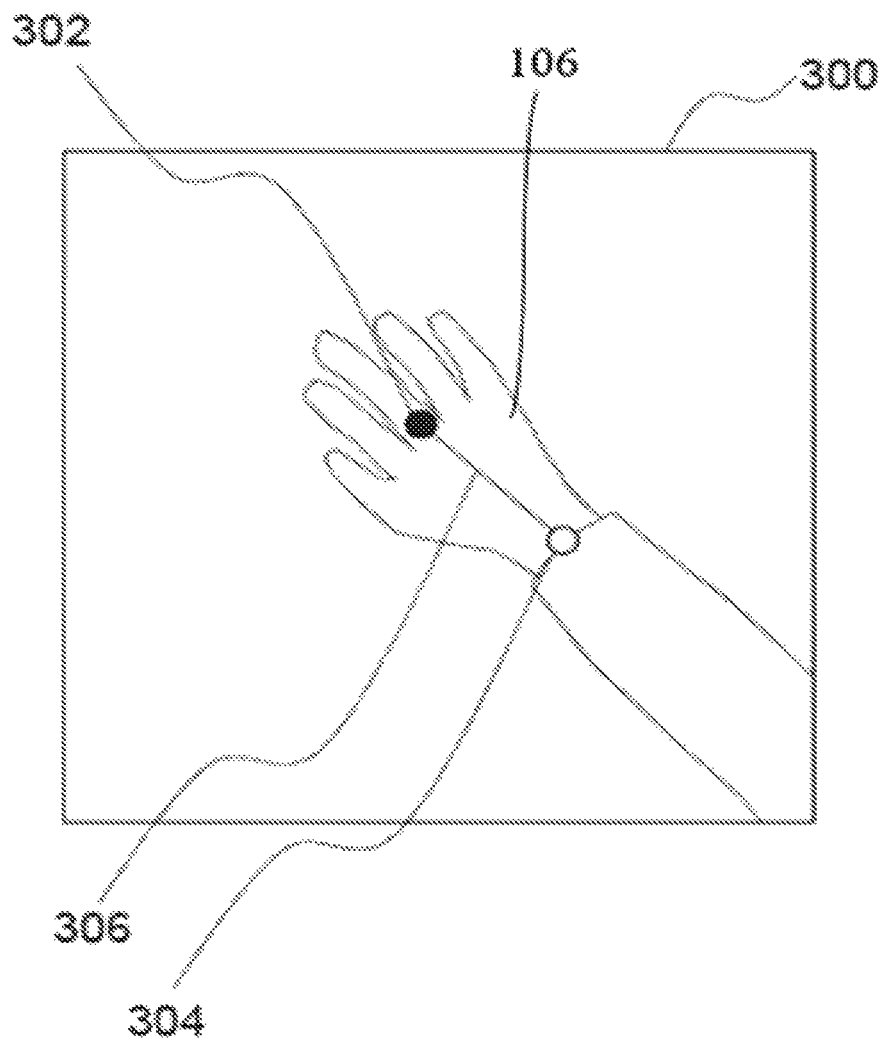
FIG. 3A shows a representation of an image, which may be a photograph or digital image, of an exemplary object to be imaged by an imaging device according to one aspect of the present disclosure.

FIG. 3A is an image 300 depicting an example of the object 106 to be imaged using an imaging device 100. In the example shown in FIG. 3A, the object 106 is a human hand; however, in other examples, the object 106 may be another anatomical feature of a human or animal, or any other object.

In the example shown in FIG. 3A, the controller 110 may determine a first position of a predetermined feature 302 corresponding to a knuckle joint of the hand and a second position of a predetermined feature corresponding to a wrist joint of the hand.

Also shown in FIG. 3A is a line 306 joining the first position of a predetermined feature 302 and the second position of a predetermined feature 304.

Figure 3B:
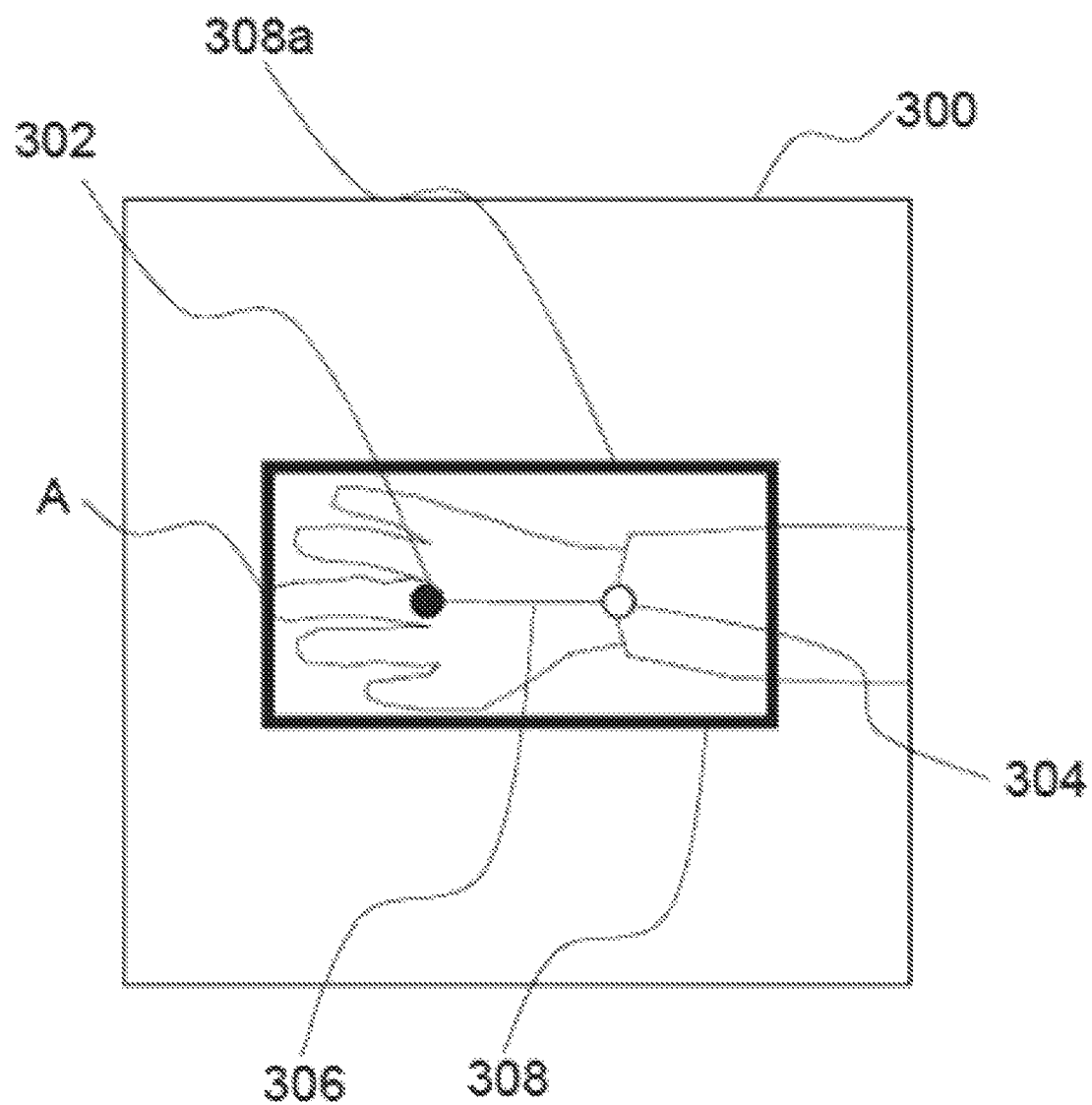
FIG. 3B shows a representation of an image, which may be a photograph or digital image, of an exemplary object to be imaged by an imaging device according to one aspect of the present disclosure.

As shown in FIG. 3B, based on an angle of that line, the controller 110 may rotate the image 300 such that an edge 308a of the image 300 is aligned with the object 106 to be imaged by the imaging device 100. The boundary box 308 is then determined as described above with reference to FIG. 2. For example, in the case where the object 106 to be imaged is a human hand, an edge of the boundary box 308 may be arranged to be parallel with a longitudinal axis of the hand, as defined by the line 306 joining the knuckle joint of the middle finger with the center of the wrist. In another example, in the case where the object 106 to be imaged is a human foot, an edge of the boundary box 308 may be arranged to be parallel with a longitudinal axis of the foot, as defined by a line joining the joint between the middle toe and the center of the ankle.

Aligning the boundary box 308 with the object 106 to be imaged in this way, in some examples, minimizes the area that is exposed to radiation that does not contain the object 106 so as to minimize the amount of radiation required to generate a useful image.

Figure 3C:
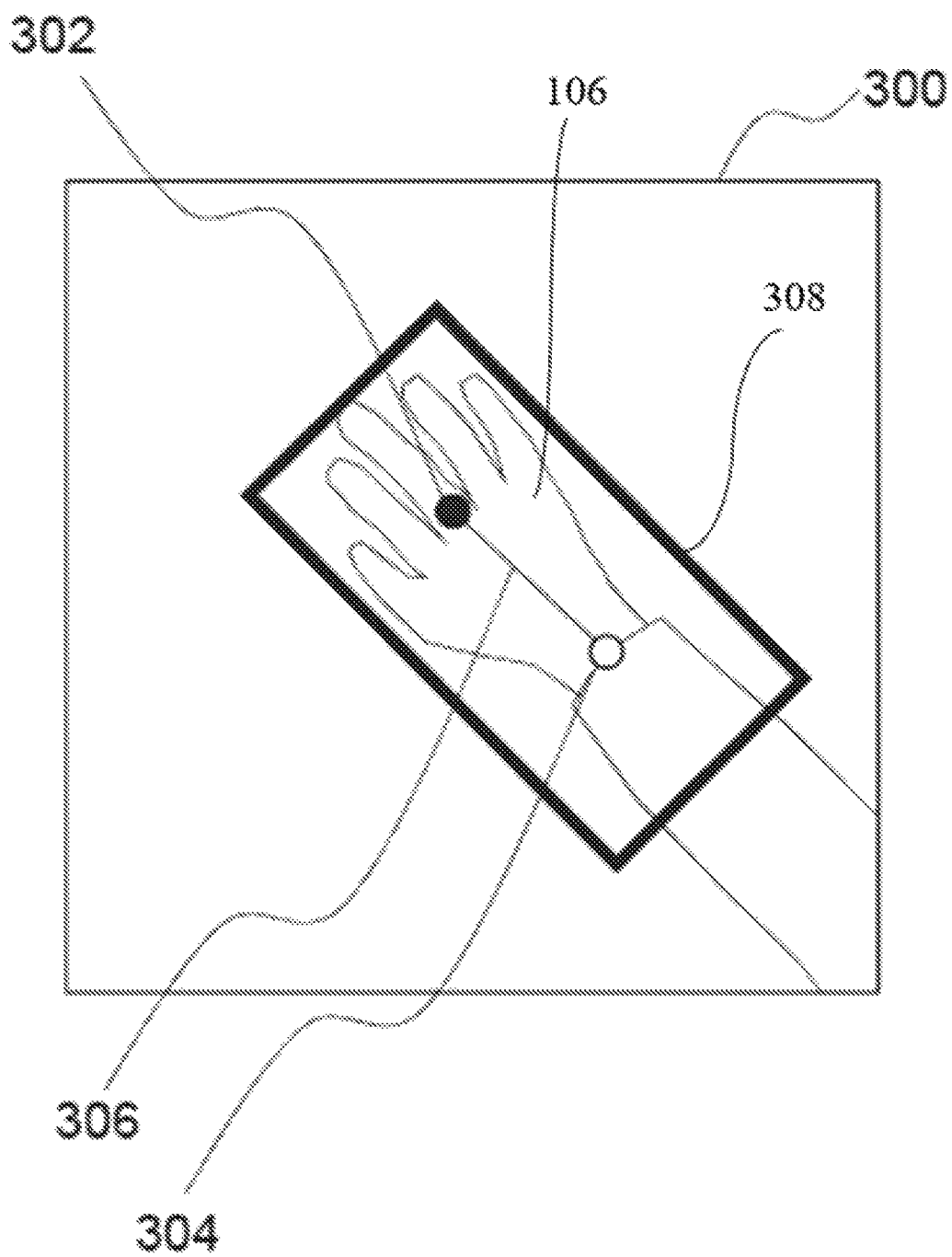
FIG. 3C shows a representation of an image, which may be a photograph or digital image, of an exemplary object to be imaged by an imaging device according to one aspect of the present disclosure.

As shown in FIG. 3C, once the boundary box determined for the image is aligned such that the image 300 is aligned with the object 106 to be imaged by the imaging device 100, the image 300 may be rotated again to its original orientation such that the boundary box is aligned and oriented with the radiation source unit 101. As the camera 116 is connected to (and moves with) the radiation source unit 112, the controller 110 may then determine a mapping between coordinates defining the boundary box in the image 300 and the one or more parameters of the radiation source unit 101, because the image is aligned with the radiation source unit 101.

In applications such as medical imaging, proper diagnosis often relies on complete imaging of a body part. Omission of any area, no matter how small the area, may result in an unusable image that must be retaken. For example, if an image of an injured hand omits the fingertips, the image may need to be repeated to include the fingertips. In applications that use ionizing radiation, such as X-ray imaging, repeating the imaging process exposes the subject to additional, potentially harmful, radiation. However, adding a large margin around an object 106 to be imaged may also be undesirable, as again it may result in additional exposure to radiation since the amount of radiation required to generate a useful image may be higher. Furthermore, adding a large margin around an object 106 to be imaged may unnecessarily expose other parts of the object 106 to radiation. For example, if the object 106 is a body part of a human subject, adding a larger than necessary margin may expose other body parts to radiation. In some cases, these other body parts may be more sensitive (e.g. prone to cellular mutation) than the body part of the object 106 to be imaged.

In order to optimize the boundary box 308 to image an area that includes all of the object 106 to be imaged but minimizes excess exposure to radiation, the boundary box 308 determined by the method 200 described above with reference to FIG. 2 may be further refined on the basis of information provided in the first image.

In some examples, the controller 110 may distinguish between a background portion of the first image and a foreground portion of the first image based on the one or more image channels. This may enable, for example, the controller 110 to set an initial constraint on the area of the image that is of interest (i.e. the area of the image that is likely to contain the object 106 to be imaged by the imaging device 100).

In the case of an image produced by a 2D camera (i.e. having only color channels) the controller 110 may distinguish between foreground and background on the basis of a difference in color. Typically, the object 106 to be imaged is located on the imaging platform 108 when the first image 300 is taken. The imaging platform 108 typically has a uniform appearance and color (which may be known) which enables the controller 110 to identify portions of the image which are background and to distinguish the object 106 in the foreground from the background.

Similarly, in the case of an image produced by a 3D camera, the controller may distinguish between background and foreground on the basis of a difference in color (or intensity) and may additionally or alternatively distinguish between background and foreground on the basis of a difference in depth. In particular, the imaging platform 108 is typically flat and at a known depth and the controller 110 may determine that locations at that known depth are background and location forward of that depth are foreground.

In some examples, the controller 110 may determine an initial boundary box 308 and refine the initial boundary box 308 to ensure that the boundary box 308 encompasses all features in the foreground portion of the first image but does not encompass excessive amounts of the background portion of the first image.

Figure 4:
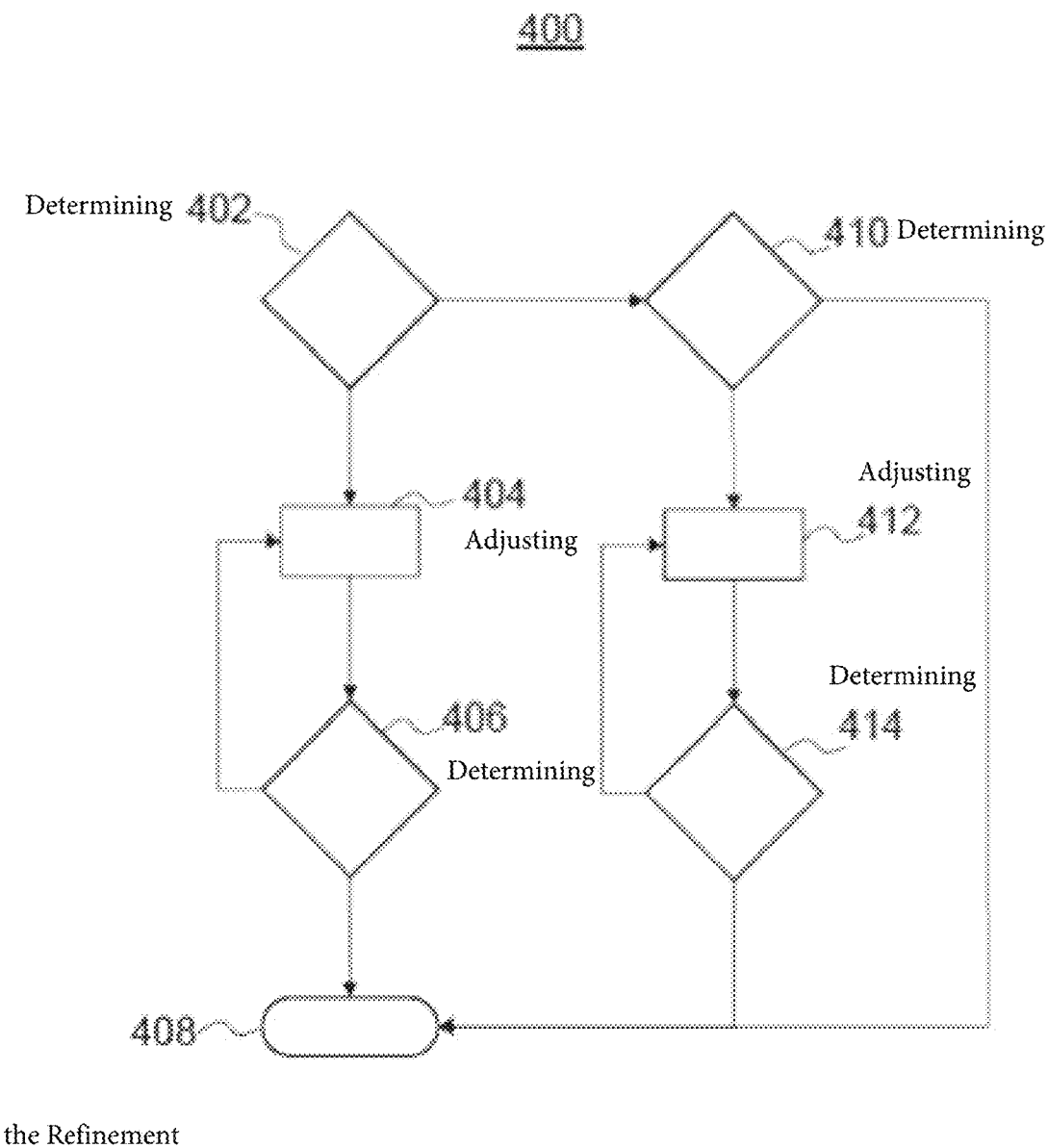
FIG. 4 shows a workflow diagram illustrating a method according to one aspect of the present disclosure.

FIG. 4 shows a method 400 by which the initial boundary box 308 may be refined. In most medical imaging applications, the object 106 to be imaged is connected to the rest of the subject's body (for example, a hand is connected to an arm by a wrist). Accordingly, in such cases, there will always be some part of the foreground portion of the image that intersects the boundary box 308. In the example shown in FIG. 3B, that foreground portion of the image intersects the boundary box 308 at an edge at the point A; however, depending on the positioning of the object 106 to be imaged that foreground portion of the image may intersect the boundary box 308 on another edge of the boundary box 308.

In such examples, the controller 110 may identify a first part of the object 106 to be imaged, and determine the boundary box so as to encompass that part. For example, the controller may identify that one of the predetermined features is at a distal feature of the object 106 to be imaged (e.g. a knuckle joint of a hand) with respect to a proximal feature (e.g. a wrist joint connecting the hand to an arm), and identify a distal end of the object to be imaged (i.e. the outermost portion of the object to be imaged), such as the fingertips of a hand, on the basis of the first position. The controller 110 may then determine the boundary box to ensure that the distal end of the object is encompassed by the boundary box. For example, one or more of three sides of the boundary box 308 near the finger region (determined from the detected positions of predetermined features) may be moved to extend the area defined by the boundary box.

At block 402, the controller 110 determines whether a portion of the foreground portion of the first image, distal to an identified position of a predetermined feature that relates to a distal feature (referred to as a "first part" below), intersects the boundary box 308, for example as shown at point A in FIG. 3B.

If, at block 402, the controller 110 determines that the first part intersects the boundary box 308, the controller 110 proceeds to block 404.

At block 404, the controller 110 adjusts one or more edges of the boundary box 308 to enlarge an area of the first image encompassed by the boundary box 308 before proceeding to block 406. For example, the controller 110 may move each of the three edges (308*a*, 308*b*, 308*c*) of the boundary box 308 closest to a distal feature of the object 106 to be imaged away from the corresponding position of the predefined feature by a predefined amount.

At block 406, the controller 110 determines again whether the first part intersects the boundary box 308.

If at block 406 it is determined that the first part intersects the boundary box 308, the controller 110 returns to block 404 and adjusts one or more edges of the boundary box 308 to enlarge an area of the first image encompassed by the boundary box 308, subsequently returning again to block 406.

If, at block 406, the controller 110 determines that no portion of the first part intersects the boundary box 308, the controller 110 proceeds to block 408 to end the refinement method 400.

Figure 5:
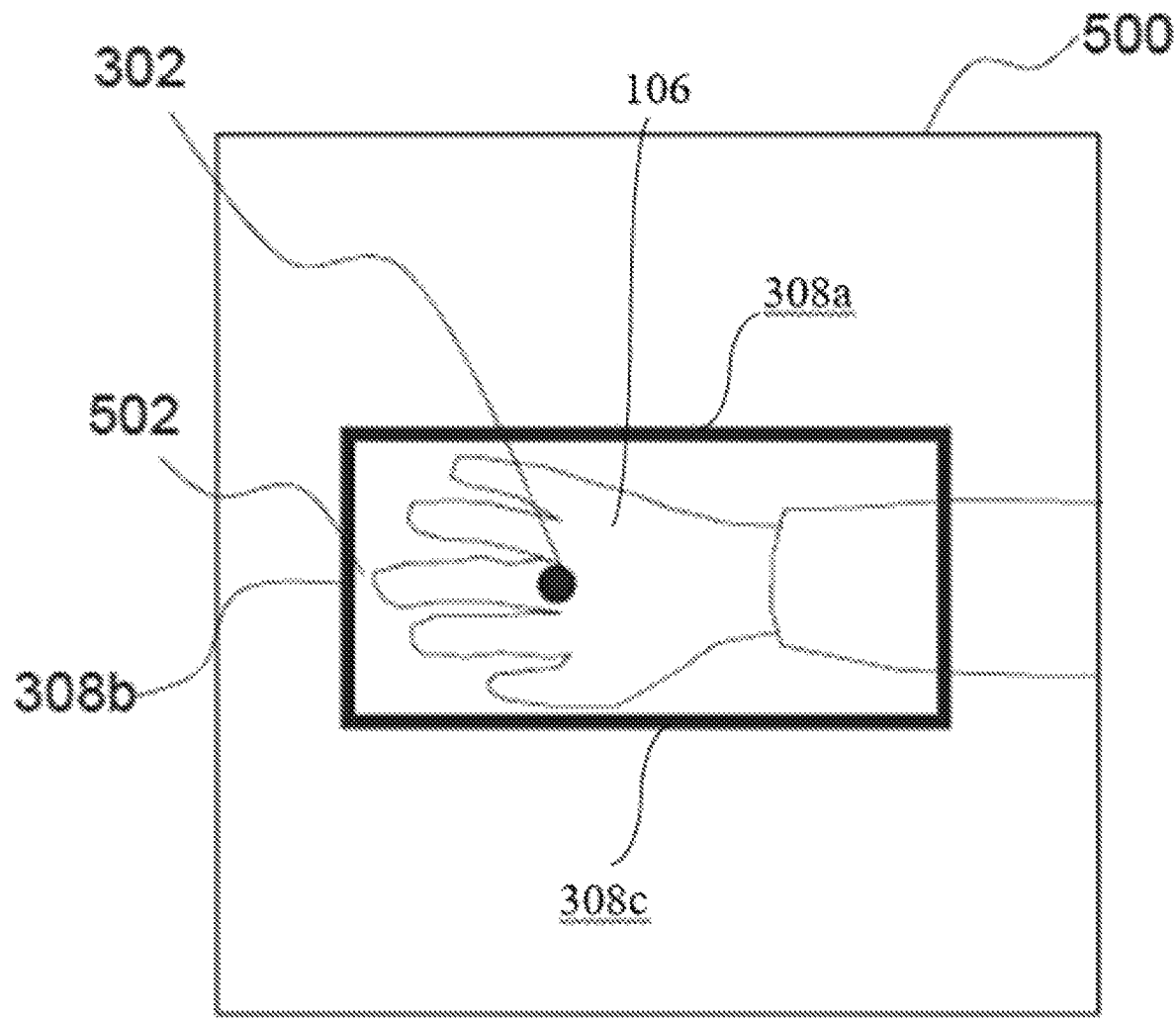
FIG. 5 shows a representation of an image, which may be a photograph or digital image, of an exemplary object to be imaged by an imaging device according to one aspect of the present disclosure.

FIG. 5 shows an example of an image 500 after the controller 110 has refined the boundary box 308 shown in FIG. 3B. After determining that an edge 308*b* of the boundary box 308 intersects with the first part of the object 106 at point A as shown in FIG. 3B, the controller 110 has refined the boundary box 308 by adjusting the edge 308*b* of the boundary box 308. With the refined boundary box 308 there is a region 502 of background between the foreground (the object 106) and the boundary box 308. This ensures that no part of the distal part of the object 106 is not imaged when the one or more parameters of the radiation source unit 101 and/or the collimator are controlled on the basis of the defined boundary box 308.

If, however, at block 402 the controller 110 determines that no portion of the first part intersects the boundary box 308, the controller may proceed to block 410.

At block 410, the controller 110 determines whether there is a background portion of the first image between the first part and the boundary box 308 that exceeds a threshold amount.

Figure 6:
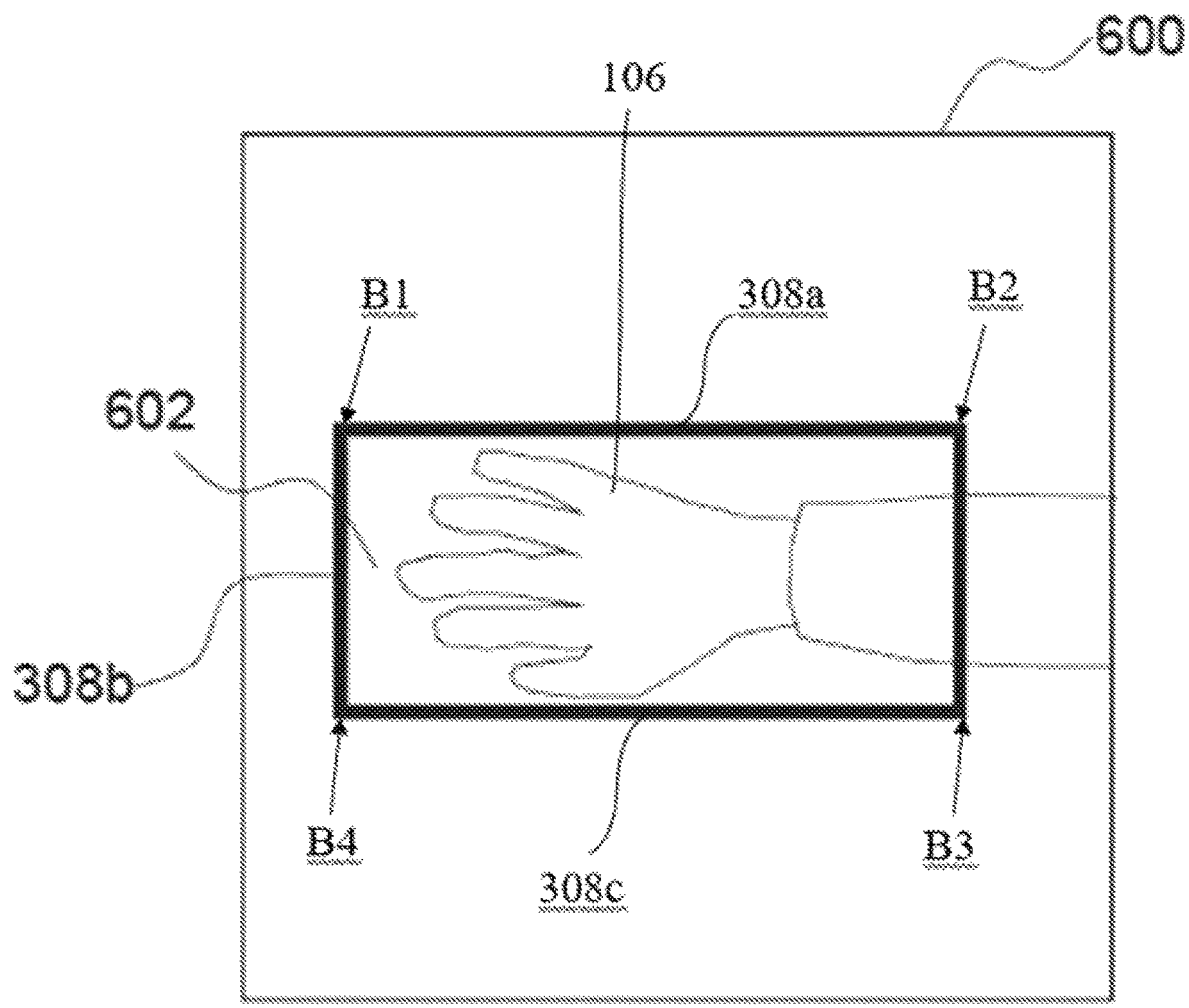
FIG. 6 a representation of an image, which may be a photograph or digital image, of an exemplary object to be imaged by an imaging device according to one aspect of the present disclosure.

For example, FIG. 6 shows an example of an image 600 for which the controller 110 has determined that in the region 602, there is a background portion of the first image, between the foreground portion of the first image and the boundary box 308, which exceeds a threshold amount.

If, at block 410, the controller 110 determines that there is not a background portion of the first image, between the foreground portion of the first image and the boundary box 308, which exceeds a threshold amount, then the controller proceeds directly to block 408.

If, however, the controller 110 determines that there is a background portion of the first image, between the foreground portion of the first image and the boundary box 308, which exceeds a threshold amount, then the controller 110 proceeds to block 412.

At block 412, the controller 110 adjusts one or more edges of the boundary box 308 to reduce an area of the first image encompassed by the boundary box 308. For example, the controller 110 may move one or more of the three edges 308a, 308b, 308c closest to a distal feature of the object 106 to be imaged towards the corresponding position of the predefined feature if an amount of background portion between the foreground portion and the respective edge of the boundary box exceeds a threshold amount.

At block 414, the controller 110 again determines whether there is a background portion of the first image between the first part and the boundary box 308 that exceeds a threshold amount.

If, at block 414, the controller 110 determines that there is a background portion of the first image, between the foreground portion of the first image and the boundary box 308, that exceeds a threshold amount, then the controller 110 returns to block 412 and again adjusts one or more edges of the boundary box 308 to reduce an area of the first image encompassed by the boundary box 308 before proceeding again to block 414.

If, however, at block 414, the controller 110 determines that the amount of background portion of the first image, distal to an identified distal feature, between the first part and the boundary box 308, is below the threshold amount, then the controller 110 proceeds to block 408 to end the refinement process 400. By performing steps 410 to 414 on the image 600 shown in FIG. 6, the controller 110 can reduce the region 602 of background between the foreground and the boundary box 308 to adjust the boundary box 308 as shown in FIG. 5. This ensures that while no part of the distal part of the object 106 is not imaged, the object 106 to be imaged is not unnecessarily exposed to excess radiation.

FIG. 6 shows an example of an image 600 for which the controller 110 has refined the boundary box 308 using the method 400 described with reference to FIG. 4 to encompass all of the portions of the object 106 to be imaged that are of interest but to minimize a region 602 of background between the foreground and the boundary box 308.

In some examples, where the object 106 is not connected to another object that is not to be imaged, the method 400 may be applied to all identified predetermined features of the object 106, rather than just a first (e.g. distal) part.

Furthermore, if the controller 110 identifies that a position of a predetermined feature relates to a proximal feature (such as a wrist of a human subject), the controller may, in relation to that predetermined feature, dispense with the method 400 described with reference to FIG. 4 in relation to the proximal feature. In doing so, the controller 110 may avoid unnecessarily expanding the boundary box to encompass parts of the subject that are, for diagnostic purposes, not of interest, but by which the object 106 to be imaged (e.g. a hand of the subject) is connected to the rest of the subject's body.

In some examples, the controller 110 may adjust all edges of the boundary box 308. In other examples, the controller 110 may adjust only portions of the boundary box 308 for which a portion of the foreground meets the boundary box 308.

The method 400 described above with reference to FIG. 4 comprises steps in which the controller 110 adjusts edges of the boundary box 308 to enlarge the area of the boundary box and steps in which the controller 110 adjusts edges of the boundary box to reduce the area of the boundary box. However, in some examples, the controller 110 may only adjust edges of the boundary box to enlarge the area of the boundary box or only adjusts edges of the boundary box to reduce the area of the boundary box.

In some examples, as shown in FIGS. 3A to 3C and FIGS. 5 and 6, the boundary box defines an area having four sides. The determination of the boundary box may comprise determining a dimension of the area. For example, the controller 110 may determine lengths of one or more sides of the area and/or a dimension across the area, such as a length of a diagonal dimension of a rectangular area or dimensions of the major and minor axes of an elliptical area, for example.

Figure 7:
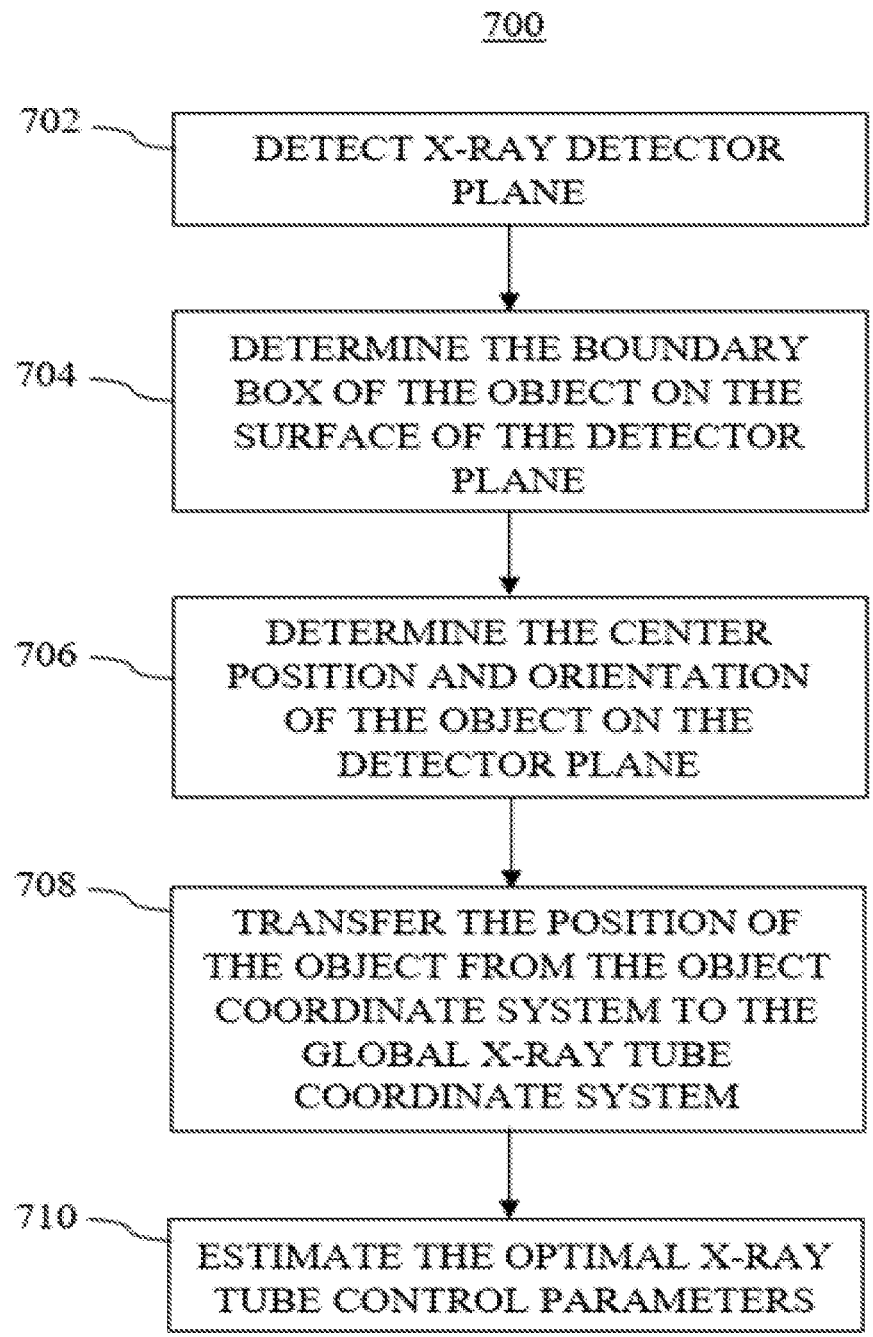
FIG. 7 is a flowchart presenting the method for X-ray tube scanner automation for acquiring X-ray scans of an object, such as a body part of a human or an animal subject (e.g. a hand, a foot, a paw, etc.), placed on a detector plane.

Referring to the flow chart 700 shown in FIG. 7, in one embodiment of the present disclosure, an automated X-ray scanning of an object 106, such as a body part of a human or an animal subject (e.g., a hand, a foot, a paw, etc.), placed on a detector plane of an X-ray tube scanner is disclosed.

At block 702, with the object 106 placed on the top surface of the X-ray detector 108, the controller 110 detects the X-ray detector plane. This can be accomplished using the method disclosed in U.S. patent application Ser. No. 15/437, 797, filed on Feb. 21, 2017, the contents of which are incorporated herein by reference. In that method visual markers are placed at each corner of the X-ray detector 108 and the camera 116 produces an image of the markers to detect the X-ray detector plane which includes the controller 110 determining the X-ray detector's position and orientation in the camera's coordinate system. Once the controller 110 detects the X-ray detector plane, the X-ray projection direction for the X-ray source 102 and collimator 104 can be aligned with the normal vector of the X-ray detector plane surface.

At block 704, the controller 110 determines the boundary box 308 of the object on the surface of the detector plane according to the detailed description provided above in connection with the FIGS. 1-6.

At block 706, with the boundary box 308 for the object 106 to be imaged (e.g. a hand or a foot) determined, the center position and the orientation (the pose) of the object 106 on the plane of the imaging platform 108 (i.e. the detector plane) can be estimated which would allow the controller 110 to be able to aim and align the X-ray collimator tube properly to image the object 106. Because the object 106 is placed on the top surface of the X-ray detector 108, and the 6-degrees-of-freedom (6-DOF) pose of the X-ray detector 108 has been determined by the X-ray detector plane detection process from U.S. patent application Ser. No. 15/437,797, determining the location and the pose of the object 106 placed on the top surface of the X-ray detector 108 is reduced to a 3-DOF problem. Thus, we only need to estimate the object's boundary box 308 on the X-ray detector's surface. In other words, the method of determining the boundary box 308 of the object provided above in connection with the FIGS. 1-6 finds the object's center position (2-DOF) and its in-plane orientation (1-DOF) on the X-ray detector plane.

The plane of the imaging platform 108 will be referred to hereinafter as "the detector plane." First, we transfer the coordinate of the four corner points B1, B2, B3, and B4 of the boundary box 308 (labeled in FIG. 6) from the camera coordinate system to the detector plane coordinate system. By enforcing the third dimension (i.e., the z dimension in the detector plane coordinate system's x, y, z dimensions with x and y being in-plane of the detector plane and z dimension being orthogonal to the detector plane) to zero, we ensure these corner points are on the detector plane surface.

Next, we can calculate the transformation from the object (hand/foot 106) coordinate system to the detector plane coordinate system as follows. Denoting these four corners of the object boundary box transferred to the detector plane surface as $\{P_k^D\}_{k=1}^4$, the transformation involves one in-plane rotation and one in-plane translation. Without any loss of generality, we can use the first two corner points as the x-axis of the object coordinate system: $=[v_x\ v_y\ 0]^T = \overrightarrow{P_1^D P_2^D}/\|\overrightarrow{P_1^D P_2^D}\|$. Then the rotation matrix R can be derived as $$R = \begin{bmatrix} v_x & -v_y & 0 \\ v_y & v_x & 0 \\ 0 & 0 & 1 \end{bmatrix}.$$

The translation vector will be the center of the transferred corners: $P_C^D = E\{P_k^D\}$, where $E\{\ \}$ is the expectation (average operator). This translation vector represents the center position of the boundary box 308 (and thus, in turn, the object 106) and its orientation on the detector plane. Therefore, the transformation can be written as a 4×4 matrix, where the rotation matrix R forms the first 3×3 sub-matrix, translation vector forms the right 3×1 sub-matrix, lower left is a 1×3 zero vector, and lower right is the scalar 1:

$$M_{OD} = \begin{bmatrix} R & P_C^D \\ 0_{1\times 3} & 1 \end{bmatrix}.$$

With this transformation, we can transfer any point $P_O$ on the object coordinate system to the global X-ray tube coordinate system via the current X-ray tube control parameters (i.e., the initial X-ray tube control parameters before the X-ray tube and the object are not aligned) and arrive at a corresponding point $P_G$ on the global X-ray tube coordinate system:

$$P_G = M_{LG} M_{CL} M_{DC} M_{OD} P_O,$$

where $M_{DC}$ is the transformation from the detector plane coordinate system to the camera coordinate system, $M_{CL}$ is the transformation from the camera coordinate system to the X-ray collimator light field coordinate system derived from kinematic calibration, and $M_{LG}$ is the transformation from the X-ray collimator light field coordinate system to the global X-ray tube coordinate system derived from the current X-ray tube control parameters. Thus, at box 708, we transfer the center position and orientation of the object from the object's coordinate system to the X-ray tube's coordinate system. The center position of the object expressed in the X-ray tube's coordinate system is where the X-ray tube should be aimed in order to produce a desired X-ray scan image of the object.

Then, at box 710, we estimate one or more of the optimal X-ray tube control parameters such that the light field emitted from the X-ray collimator center is centered at the point of interest, represented by the center position of the object in the global X-ray tube coordinate system, $P_G$:

$$M^*_{LG} = \operatorname{argmin}_{M_{LG}} \|M_{LG} P_L - P_G\|_2,$$

where the point $P_L$ is the desired light field center in the tube collimator coordinate system. The optimal $M^*_{LG}$ transformation can be calculated by non-linear least squares and the corresponding tube control parameters can be derived based on inverse kinematics of the tube robotic system's mechanical kinematic chain. For the collimator size it can be set to the distance between the corner points of the boundary box. That is, $\|\overrightarrow{P_1^D P_2^D}\|$ and $\|\overrightarrow{P_1^D P_4^D}\|$, respectively. The one or more of the X-ray tube control parameters comprise a position and/or an orientation of the X-ray tube and/or one or more X-ray collimator settings of the collimator 104 of the X-ray tube 101.

With the method of the present disclosure implemented, the X-ray tube 101 can be automatically controlled to acquire X-ray images of the region of interest in the object 106. In particular, the position and orientation of the X-ray tube is automatically controlled to align the X-ray tube with the selected region of interest. In one embodiment, the X-ray tube can be automatically guided to be aligned with a particular target location because the relationships between the coordinate systems of the X-ray tube 101, the 3D camera 116, and the X-ray detector 108 are established. Once the X-ray tube is aligned with the selected region of interest, one or more X-ray images are acquired of the region of interest using the X-ray tube.

Once the X-ray tube is automatically guided to a position and orientation corresponding to the selected region of interest and the region of interest of the object 106 is scanned by the X-ray tube to acquire an X-ray image, the X-ray image can be output by displaying the X-ray image on a display screen, by printing a physical copy of the X-ray image, and/or storing the X-ray image in a memory or storage unit of a computer system.

Figure 8:
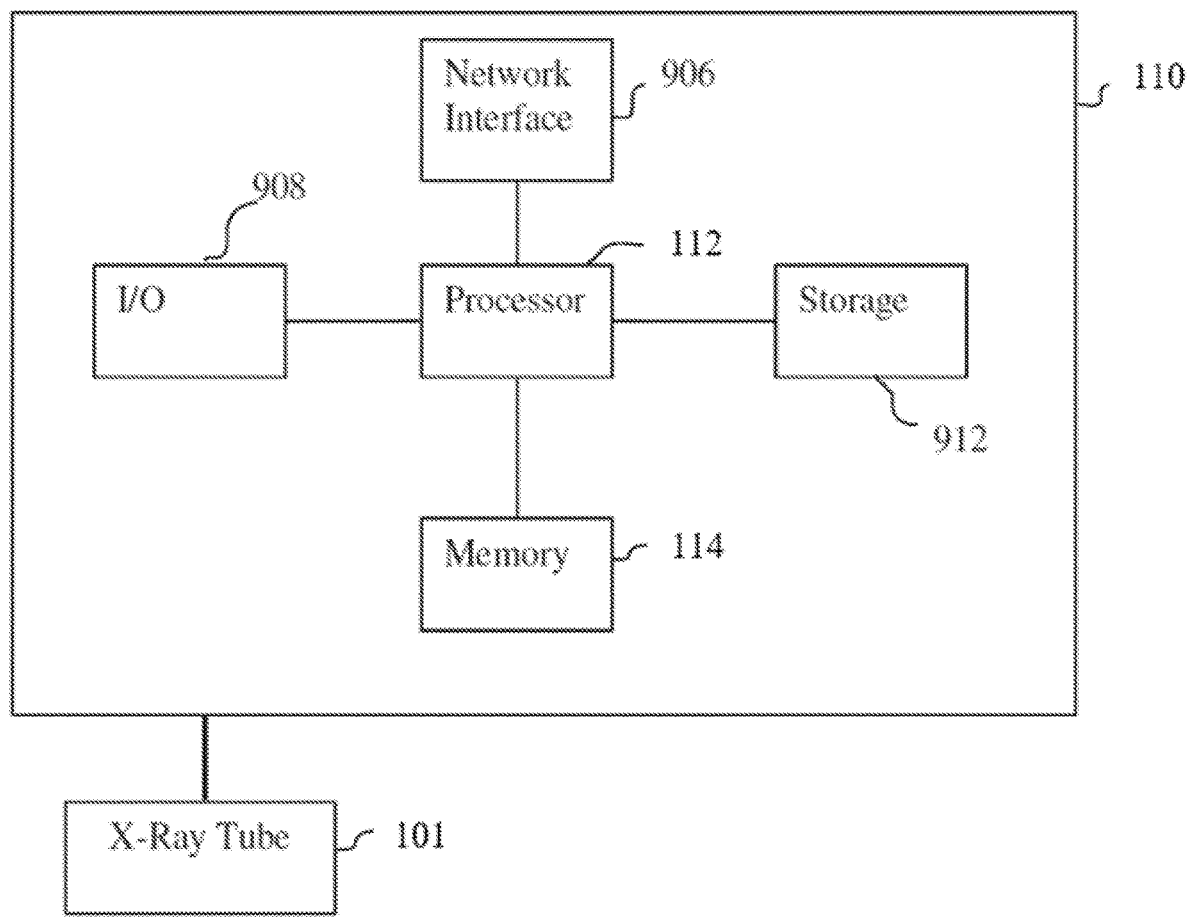
FIG. 8 is a high-level block diagram of a computer capable of implementing the methods disclosed herein.

The above-described method for X-ray tube scanner automation can be implemented on a computer controller 110 using well-known computer processors, memory units, storage devices, computer software, and other components. A high-level block diagram of the computer controller 110 is illustrated in FIG. 8. Computer controller 110 contains a processor 112, that controls the overall operation of the X-ray tube scanner 100 by executing computer program instructions that define such operation. The computer program instructions may be stored in a non-transitory computer readable data storage medium 912 (e.g., magnetic disk, flash memory chip(s), etc.) and loaded into an on-board memory 114 when execution of the computer program instructions is desired. Thus, the steps of the methods disclosed herein can be defined by the computer program instructions stored in the memory 114 and/or storage 912 and controlled by the processor 112 executing the computer program instructions. The X-ray tube 101 can be connected to the computer controller 110. The X-ray tube 101 and the computer controller 110 may be directly connected or may communicate through a network or other wireless communication protocol. The computer controller 110 can communicate with the X-ray tube 101 to control the positioning and orientation of the X-ray tube 101 and to control X-ray image acquisition by the X-ray detector 108. X-ray images acquired by the X-ray detector 108 can be input to the computer controller 110. The computer controller 110 also includes one or more network interfaces 906 for communicating with other devices via a network. The computer controller 110 also includes other input/output devices 908 that enable user interaction with the computer controller 110 (e.g., display, keyboard, mouse, speakers, buttons, etc.). One skilled in the art will recognize that an implementation of an actual computer could contain other components as well, and that FIG. 8 is a high level representation of some of the components of such a computer for illustrative purposes.

The foregoing detailed description is to be understood as being in every respect illustrative and exemplary, but not restrictive, and the scope of the invention disclosed herein is not to be determined from the detailed description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

We claim:

1. A method for X-ray tube scanner automation, wherein the X-ray tube scanner comprises an X-ray tube and an X-ray detector, the method comprising:
   acquiring, by a three-dimensional camera that includes a camera coordinate system, a three-dimensional image of an object placed on the X-ray detector, the X-ray detector including an X-ray detector coordinate system;
   identifying the X-ray detector's plane in the three-dimensional image;
   generating a boundary box of the object on the X-ray detector, the boundary box comprising four corner points;
   determining the object's center position and orientation on the X-ray detector's plane;
   transferring the four corner points of the boundary box from the camera coordinate system to the X-ray detector's coordinate system;
   calculating a transformation function from an object coordinate system to the X-ray detector coordinate system using one in-plane rotation and in-plane translation and the object's center position and orientation;
   transferring, using the transformation function, the object's center position from the object's coordinate system to a coordinate system of the X-ray tube; and
   estimating X-ray tube control parameters for aligning an X-ray field emitted from a center of a collimator of the X-ray tube to the object's center position in the coordinate system of the X-ray tube.

2. The method of claim 1, wherein the X-ray tube scanner determining the boundary box of the object to be imaged on the X-ray detector comprises:
   receiving image data representing a first image of the object to be imaged using the X-ray tube to form a second image;
   detecting a plurality of positions of respective predetermined features in the first image;
   determining the boundary box of an imaging area of the object to be imaged on the basis of the detected positions; and
   controlling one or more parameters of the X-ray tube on the basis of the determined boundary box.

3. The method of claim 2, further comprising:
   determining an object size and/or an object orientation of the object to be imaged on the basis of the detected positions.

4. The method of claim 3, further comprising:
   determining the object orientation on the basis of an angle of a line intersecting two or more of the detected positions; and
   orienting the boundary box of the imaging area of the object to correspond with the object orientation.

5. The method of claim 1, wherein the X-ray tube control parameters comprise a position of the X-ray tube and/or one or more collimator settings of the collimator of the X-ray tube.

6. An X-ray tube scanner system comprising:
   an X-ray tube including a coordinate system;
   a three-dimensional camera that includes a camera coordinate system;
   an X-ray detector that includes an X-ray detector coordinate system; and
   a system controller, wherein the system controller comprising a processor, and a non-transitory computer readable medium storing computer program instructions for operating the X-ray tube scanner,
   wherein the computer program instructions when executed by the processor cause the processor to perform operations comprising:
   acquiring using the three-dimensional camera a three-dimensional image of an object placed on the X-ray detector;
   detecting the X-ray detector's plane in the three-dimensional image;
   generating a boundary box of the object to be imaged on the X-ray detector, the boundary box comprising four corner points;
   determining the object's center position and orientation on the X-ray detector's plane;
   transferring the four corner points of the boundary box from the camera coordinate system to the X-ray detector's coordinate system;
   calculating a transformation function from an object coordinate system to the X-ray detector coordinate system using one in-plane rotation and in-plane translation and the object's center position and orientation;
   transferring, using the transformation function, the object's center position from the object's coordinate system to the X-ray tube's coordinate system; and
   estimating X-ray tube control parameters for aligning an X-ray field emitted from the X-ray tube's collimator to the object's center position in the coordinate system of the X-ray tube.

7. The X-ray tube scanner system of claim 6, wherein the X-ray tube scanner determining the boundary box of the object to be imaged on the X-ray detector comprises:
   receiving image data representing a first image of the object to be imaged using the X-ray tube to form a second image;
   detecting a plurality of positions of respective predetermined features in the first image;
   determining the boundary box of an imaging area of the object to be imaged on the basis of the detected positions; and
   controlling one or more parameters of the X-ray tube on the basis of the determined boundary box.

8. The X-ray tube scanner system of claim 7, wherein the operation performed by the processor further comprising:
determining an object size and/or an object orientation of the object to be imaged on the basis of the detected positions.

9. The X-ray tube scanner system of claim 8, wherein the operation performed by the processor further comprising:
determining the object orientation on the basis of an angle of a line intersecting two or more of the detected positions; and
orienting the boundary box of the imaging area of the object to correspond with the object orientation.

10. The X-ray tube scanner system of claim 6, wherein the X-ray tube control parameters comprise a position of the X-ray tube and/or one or more collimator settings of the collimator of the X-ray tube.

11. A non-transitory computer readable medium storing computer program instructions for X-ray tube scanner automation, wherein the X-ray tube scanner comprising an X-ray tube and an X-ray detector, the computer program instructions when executed by a processor cause the processor to perform operations comprising:
acquiring, by a three-dimensional camera that includes a camera coordinate system, a three-dimensional image of an object placed on the X-ray detector that includes an X-ray detector coordinate system;
identifying the X-ray detector's plane in the three-dimensional image;
generating a boundary box of the object on the X-ray detector, the boundary box comprising four corner points;
determining the object's center position and orientation on the X-ray detector's plane;
transferring the four corner points of the boundary box from the camera coordinate system to the X-ray detector's coordinate system;
calculating a transformation function from an object coordinate system to the X-ray detector coordinate system using one in-plane rotation and in-plane translation and the object's center position and orientation;
transferring, using the transformation function, the object's center position from the object's coordinate system to a coordinate system of the X-ray tube; and
estimating X-ray tube control parameters for aligning an X-ray field emitted from a center of a collimator of the X-ray tube to the object's center position in the coordinate system of the X-ray tube.

12. The non-transitory computer readable medium of claim 11, wherein the X-ray tube scanner determining the boundary box of the object to be imaged on the X-ray detector comprises:
receiving image data representing a first image of the object to be imaged using the X-ray tube to form a second image;
detecting a plurality of positions of respective predetermined features in the first image;
determining the boundary box of an imaging area of the object to be imaged on the basis of the detected positions; and
controlling one or more parameters of the X-ray tube on the basis of the determined boundary box.

13. The non-transitory computer readable medium of claim 12, further comprising:
determining an object size and/or an object orientation of the object to be imaged on the basis of the detected positions.

14. The non-transitory computer readable medium of claim 13, further comprising:
determining the object orientation on the basis of an angle of a line intersecting two or more of the detected positions; and
orienting the boundary box of the imaging area of the object to correspond with the object orientation.

15. The non-transitory computer readable medium of claim 11, wherein the X-ray tube control parameters comprise a position of the X-ray tube and/or one or more collimator settings of the collimator of the X-ray tube.

* * * * *